US006184247B1

(12) United States Patent
Schneider

(10) Patent No.: US 6,184,247 B1
(45) Date of Patent: Feb. 6, 2001

(54) METHOD OF INCREASING CELL RENEWAL RATE

(75) Inventor: Louise M. Schneider, Rockford, MI (US)

(73) Assignee: Amway Corporation, Ada, MI (US)

( * ) Notice: Under 35 U.S.C. 154(b), the term of this patent shall be extended for 0 days.

(21) Appl. No.: 09/316,161

(22) Filed: May 21, 1999

(51) Int. Cl.[7] .......................... A01N 43/08; A01N 43/50
(52) U.S. Cl. .............................. 514/474; 424/401
(58) Field of Search ............................ 424/401; 514/474

(56) References Cited

U.S. PATENT DOCUMENTS

| | | |
|---|---|---|
| Re. 33,993 | 7/1992 | Grollier et al. . |
| 3,012,942 | 12/1961 | Morse . |
| 3,012,943 | 12/1961 | Morse . |
| 3,086,915 | 4/1963 | Morse . |
| 4,014,995 | 3/1977 | Juliano et al. . |
| 4,238,509 | 12/1980 | Evans et al. . |
| 4,278,656 | 7/1981 | Nagai et al. . |
| 4,363,815 | 12/1982 | Yu et al. . |
| 4,369,174 | 1/1983 | Nagai et al. . |
| 4,548,728 | 10/1985 | Franklin . |
| 4,722,843 | 2/1988 | Vinson . |
| 4,806,365 | 2/1989 | Nakashima . |
| 4,851,252 | 7/1989 | Greither et al. . |
| 4,877,627 | 10/1989 | Leitz et al. . |
| 4,883,659 | 11/1989 | Goodman et al. . |
| 4,919,921 | 4/1990 | Hatae . |
| 5,091,171 * | 2/1992 | Yu et al. .............................. 424/642 |
| 5,171,571 | 12/1992 | Stephan et al. . |
| 5,262,153 | 11/1993 | Mishima et al. . |
| 5,262,162 | 11/1993 | Bormann et al. . |
| 5,281,196 | 1/1994 | Sultenfuss . |
| 5,296,500 | 3/1994 | Hillebrand . |
| 5,352,389 | 10/1994 | Gazzani . |
| 5,427,775 | 6/1995 | Sakai et al. . |
| 5,441,740 | 8/1995 | Ozlen . |
| 5,449,519 | 9/1995 | Wolf et al. . |
| 5,747,006 | 5/1998 | Dornoff et al. . |

FOREIGN PATENT DOCUMENTS

| | | |
|---|---|---|
| 195 15 609 C1 | 4/1996 | (DE) . |
| 2 597 337 | 10/1987 | (FR) . |
| 2 720 643 | 12/1995 | (FR) . |
| 62-208236 | 9/1987 | (JP) . |
| 62-208267 | 9/1987 | (JP) . |
| 2-200610 | 8/1990 | (JP) . |
| 5-207865 | 8/1993 | (JP) . |
| 7-61915 | 3/1995 | (JP) . |

OTHER PUBLICATIONS

Search results from Teltech® Literature Search Service re Skin Whiteners, Apr. 4, 1996, pp. 1–49.
*Report of a Case of Acute Infant Scurvy Treated with Acerola Jelly*, C.F. Asenjo Ph.D. and O. Gonzalez–Alvarez, M.D., 1955.

*Ascorbic Acid Content and Other Characteristics of the West Indian Cherry*, Conrado F. Asenjo and Carlos G. Moscoso, Department of Chemistry and Nutrition School of Tropical Medicine and Department of Plant Breeding, Agricultural Experiment Station, University of Puerto Rico, Food Research, vol. 15, Jan.–Dec., 1950, pp. 103–106.

*Acerola Juice Ready for Commercial Production*, Journal of Agricultural and Food Chemistry, Nov. 10, 1954, vol. 2, No. 23, p. 1155.

*Skin Lightening, A Review of melanin formation and the isolation of a new ingredient for products that minimize skin discolorations due to excessive melanin production*, Ok–Sub Lee, Eun–Joung Kim, Cosmetics & Toiletries® magazine, vol. 110, Oct. 1995, pp. 51–56.

Chemical Abstract, No. 122(21)264022r, *Kinetics Of Anthocyanin Decompostion In Acerola Juice*, Author(s): Harvey T. Chan, Jr., and Harry Y. Yamamoto, Journal: Asean Food J., 1994, vol. 9, No. 4, pp. 132–135.

Chemical Abstract, No. 121(17)198461j, *Effects Of Growth Regulators Applied At Blooming Time On Fruit Quality Of Acerola, Malpighia emerginata dc.*, Author(s) Kiyotake Ishihata and Saburo Ito, Journal: Nettai Nogyo, 1994, vol. 38, No. 2, pp. 113–118.

Chemical Abstract, No. 120(23) 297204(p) *Nutrient–Supplying Foods Containing Vitamin C*, Inventor (Author): Togo Kuroiwa; Patent: Japan Kokai Tokkyo Koho; JP 9422727 A2; dated Feb. 1, 1994.

Chemical Abstract, No. 120(17) 215777r, *Acerola Juice as Acidulant in Preparation of Frozen Desserts*, Inventor (Authors): Hiroshi Yamane; Teruaki Myazaki and Kyoshi Takada; Japan Kokai Tokyo Koho JP 93344846 A2; dated Dec. 27, 1993.

Chemical Abstract, No. 120(16) 200486w, *Dialysis System for Large Intestine, Method of Use, and Filtrate Solution Composition*, Inventor (Author): Andrew Stone, Patent: PCT International WO 9403215; dated Feb. 17, 1994.

Chemical Abstract, No. 120(11)132676f, *Volatile Constituents of Acerola*, C. Schippa, G. George, R. Fellous, Journal: Parfums, Cosmet., Aromes; 1993, vol. 113, pp. 81–84.

(List continued on next page.)

Primary Examiner—S. Mark Clardy
Assistant Examiner—Michael A. Williamson
(74) *Attorney, Agent, or Firm*—Brinks Hofer Gilson & Lione; G. Peter Nichols

(57) ABSTRACT

The present invention relates to a method of enhancing the rate of skin desquamation by incorporating an ascorbic acid derivative into a cosmetic composition suitable for application to mammalian skin. The ascorbic acid derivative is selected from the group consisting of esters of ascorbic acid, salts, and mixtures thereof. The esters are generally selected from fatty acid mono-, di-, tri-, or tetra-esters. The salts are generally selected from ascorbyl phosphates, ascorbyl sulfates, and mixtures thereof.

11 Claims, No Drawings

OTHER PUBLICATIONS

Chemical Abstract, No. 119(23)248618x, *Vitamin C–High Nutrition Supplements Preparation from Acerola Fruits*, Inventor (Author) Togo Kuroiwa, Patent: Japan Kokai Tokyo Koho JP 93207865 A2, dated Aug. 20, 1993.

Chemical Abstract, No. 118(23)2733z, *Carotenoid–Containing Emulsions for Use in Foods Without the Use of Synthetic Agents*, Inventor (Author) Lance Elliott Schilipalius, Patent: PCT International WO 9304598 A1; dated Mar. 18, 1993.

Chemical Abstract, No. 118(21) 211546a, *Calculation of Juice Content in a Diluted Fruit Juice Beverage*, Chester W. Lindsay, Journal: J. AOAC Int., 1993, vol. 76, No. 2, pp. 424–430.

Chemical Abstract, No. 118(1)5952b, *Analysis of Acerola*, Authors: Shintetu Kunlyoshi, Minoru Suzuki and Hiromichi Hayano, Journal: Kanzel Chuo Bunsekishoho; 1992, vol. 31, pp. 81–85.

Chemical Abstract, No. 117(17)169813n, *The Ascorbic Acid Contents of Fruits of Taiwan*, Authors: Huei Ing Liu, and Iuan Huei Hwang, Journal: Zhonghua Nongye Yanjiu; 1991, vol. 40, No. 3, pp. 280–290.

Chemical Abstract, No. 115(25)278390b, *Change in Vitamin C During the Fermentation of Acerola Vinegar*, Makoto Nakamura, Journal: Nippon Shokuhin Kogyo Gakkaishi, 1991, vol. 38, No. 8, pp. 691–694.

Chemical Abstract, No. 114(19)184032p, *Ascorbic Acid Content in Acerola Fruit From Different Production Regions in Relation to Degree of Maturity and Its Stability During Processing*, Author(s): Saburo Itoo, Mitsuko Aiba, Kiyotake Ishihata; Journal: Nippon Shokuhin Kogyo Gakkaishi; 1990, vol. 37, No. 9, pp. 726–729.

Chemical Abstract, No. 114(18)170990n, *Water Purifying Agent*, Inventor (Author) Norio Someya, Patent: Japan Kokai Tokyo Koho JP 90268885A2; dated Nov. 2, 1990.

Chemical Abstract, No. 110(23)211306(g), *Vinegar Enriched With Vitamin C and Its Manufacture*, Inventor (Author) Todomu Nakashima, Patent: United States Pat. No. 4,806,365 dated Feb. 21, 1989.

Chemical Abstract, No. 108(26)226675j, *Cosmetic Containing Antioxidants to Delay the Aging of Skin*, Inventor (Author) Olivier Courtin, Patent: French Patent No. FR 2597337 dated Oct. 23, 1987.

Chemical Abstract, No. 104(25)223741j, *Pesticide Tolerances for Glyphosate*, Corporate Author: United States Environmental Protection Agency, Journal: Federal Regist., 1986, vol. 51, No. 78, pp. 15325–15326.

Chemical Abstract, No. 100(9)66734g, *Pesticide Programs, Tolerances for Pesticide Chemicals in or on Raw Agricultural Commodities*, Paraquat, Corporate Author: United States Environmental Protection Agency, Journal: Fed. Regist., 1984, vol. 49, No. 4, p. 882.

Chemical Abstract, No. 72(13)65961v, *Root Development of Acerola Trees as Affected by Liming*, Authors: Ernesto Hernandez–Medina, J. Velez–Santiago, M.A. Lugo–Lopez, Journal: J. Agr. Univ. P.R., 1970, vol. 54, No. 1, pp. 57–61.

Chemical Abstract, No. 68(1)2091h, *Observations on Physical and Chemical Properties of Acerola Fruit and Puree*, Author: Brian Ian Brown, Journal: Queensl. J. Agric. Anim. Sci., 1967, vol. 23, No. 4, pp. 599–604.

Chemical Abstract, No. 67(25)115916d, *Titrimetric determination of L–Ascorbic Acid in Colored Solutions. I.V. Acerola Cherries and Their Concomitant Use in Fruit Juices*, Authors: Rudolf Fischer, G. Freise; Journal: Dtsch. Apoth.–Ztg.; 1967, vol. 107, No. 34, pp. 1175–1176.

Chemical Abstract, No. 66(21)92405z, *Factors Affecting Ascorbic Acid Content of the Acerola (Malphigia Glabra)*, Authors: H.Y. Nakasone, R.K. Miyashita, George M. Yamane, Journal: Proc. Am. Soc. Hortic. Sci., 1966, vol. 89, pp. 161–166.

Chemical Abstract, No. 66(5)18134u, *Ascorbic Acid Content of Acerola Fruits and Acerola Powder, Ascorbic Acid Determination in the Presence of Reductones*, Author: Annefies Schillinger, Journal: Z. Lebensm.–Unters. Forsch, 1966, vol. 131, No. 2.

Chemical Abstract No. 531391, Embase No. 76115593, *Therapeutic Use of 'Avena' Skin Cleansing Preparations*, Kuerner H. Karlstr. 29, Karlsruhe Germany West; Z. Hautkr. (Germany, West), 1975, 50/15 (631–635).

Chemical Abstract, No. 12064007, Pascal No. 95–0263947; *Oats: Chemistry, Technology and Potential Uses in the Cosmetic Industry*; Paton, D.; Bresciani, S.; Nam Fong Han; Hart, J.; Journal: Cosmetics and Toiletries; 1995, 110(3) 63–70 (5 p.).

Chemical Abstract, No. 00911864, Pascal No. 76–0006664; *Therapeutischer erfahrungsbericht mit der avena–reihe (Resultats therapeutiques obtenus avec les produits avena)*; Kurner H. Ankermann & Co. G.M.B.H., Friesoythe, Journal: Z. Hautkrankh, 1975, 50 (15) 631–635.

Chemical Abstract, No. 001371746; WPI Acc No: 75–21383W/13; Patent Assignee: Quaker Oats Co.; Priority Data (CC No. Date): Us 398651 (730919); US 565695 (750407).

Chemical Abstract, No. 010545082; WPI Acc No. 96–042035/05; Patent Assignee: Clarins; Priorty Data (CC No. Date); FR 946837 (940603).

Chemical Abstract, No. 010338357; WPI Acc. No. 95–240445/31; Patent Assignee: Nurture Inc; Priority Data (CC No Date); US 172485 (931223).

Chemical Abstract, No. 010002632; WPI Acc. No. 94–270343/33; Patent Assignee: (Kono) Konovalov II; Priority Data (CC No Date); SU 5016466 (911228).

Chemical Abstract, No. 009708838; WPI Acc. No. 93–402391/50; Patent Assignee: (Aero=) Aerozol sci prodn assoc; (stal=) stalgen agric firm; Priority Data (CC No Data); SU 4868052 (900921).

Chemical Abstract, No. 00362016; Derwent Accession No: 73–35329; *A New Natural Ingredient for Cosmetic Formulators*; Assignee: Quaker–Oats (Cleveland Ohio USA); Journal: Drug Cosmet. Ind., 113, No. 3, 48, 50, 52, 54, 56, 1973.

Chemical Abstract, No. 124298400; CA: 124 (22)298400u; *Formulating personal care products with hydrolyzed oat protein*; Author(s): Loncar, Clifford; Journal: Household Pers. Prod. Ind.; Date: 1996, vol. 33; No.: 3; pp. 85–87.

Chemical Abstract, No. 124269972; CA: 124(20)269972(b); *Hair and Scalp Conditioners Containing Oat Extract and Hydroxy Acids*; Inventor (Author) Onitsuka, Satoshi; Dubowoj, Polina; Assignee: Kao Corporation GMBH; Patent: Germany; DE 19515609 C1; Date: Mar. 28, 1996.

Chemical Abstract, No. 123152610; CA: 123(12)152610v; *Oat Oil Compositions with Useful Dermatological Properties*; Inventor (Author); Potter, Richard; Castro, James M.; Moffatt, Lori C.; Assignee: Nurture, Inc., Patent: Pct International; WO 9517162 A1; Date: Jun. 29, 1995; p. 36 pp.

Chemical Abstract, No. 94109095; CA: 94(14)109095b; *The Water Oat Extracts as Skin Cosmetics*, Assignee: Onodera, Hiroshi; Patent: Japan Kokai Tokkyo Koho JP 80164613; Date: Dec. 22, 1980.

Chemical Abstract, No. 88197417; CA: 88(26)197417n; *Cosmetic Ingredients*; Author(s): Miller, Aaron; Location: Kalar Lab., Chicago, Ill.; Journal: Soaps, Deterg. Toiletries Rev., Date: 1977; vol.: 7; No.: 9; pp. 21–25.

Chemical Abstract, No. 80030602; CA: 80(6)30602s; *New Natural Ingredient for Cosmetic Formulators*; Author(s): Coe, John; Juliano, Angelo; Journal: Drug Cosmet. Ind.; Date: 1973: vol.: 113; No.: 3; pp: 48, 50, 52, 54, 56.

Chemical Abstract, No. 0458058; *This Cosmetic Company Really Knows Its Oats*, Business Week, Feb. 22, 1993; p. 91; No. 3306.

Chemical Abstract, No. 008399002; WPI Acc No: 90–286003/38; *Cosmetic Acerola extract—obtd. by washing with water, removing ppte. decolouring and filtering*; Patent Assignee: (Nich–) Nichirei KK; Priority Data (CC No. Date): JP 8916185 (Jan. 27, 1989).

Chemical Abstract, No. 007353231; WPI Acc No: 87–350237/50; *Two–part skin anti–ageing cosmetic compsn.—contg. active principle hindering skin ageing due to formation and action of free radicals*; Patent Assignee: (Cour) Courtin O; (Clar–) Clarins; Priority Data: (CC No Date): FR 8788 (870000); FR 8416038 (Oct. 19, 1984).

Chemical Abstract, No. 108226675; CA: 108(26)226675j; *Cosmetic containing antioxidants to delay the aging of skin*; Application: FR 8788 (Jan. 7, 1987).

*Oats; Chemistry, Technology and Potential Uses in the Cosmetic Industry, High purity oat derivatives show potential as plant–based conditioning ingredients for skin–and hair–care*; David Paton and Sandra Bresciani; Agriculture and Agri–Food Canada, Saskatoon, SK, Canada; Nam Fong Han, Canamino, Inc., Ottawa, ON, Canada; Janice Hart, Canamino Inc., Long Island, NY, USA; Cosmetics & Toiletries Magazine, vol. 110, Mar. 1995, pp. 63–70.

* cited by examiner

METHOD OF INCREASING CELL RENEWAL RATE

BACKGROUND OF THE INVENTION

The present invention relates to a composition to enhance the rate of skin cell renewal or exfoliation and to a method of increasing the skin cell renewal rate. In particular, the present invention relates to a composition containing a skin benefit agent that includes a derivative of ascorbic acid that stimulates cell renewal but does not unduly irritate. The present invention also relates to a method of increasing the rate of skin-cell renewal by applying a composition to the skin, wherein the composition comprises an effective amount of a derivative of ascorbic acid.

The skin of humans is continually assaulted by environmental conditions such as the sun, wind, and pollution. These environmental assaults weather or age the skin causing, among other things, wrinkles, age spots and other undesirable skin conditions. In addition, the effects of natural aging also cause the skin to wrinkle.

These negative effects can be prevented or at least ameliorated by applying skin care cosmetics that contain skin benefit agents according to the present invention.

Human skin may be classified into two major parts: the outer layer or epidermis and an underlying layer or dermis. The dermis contains among other things, blood vessels, nerves, collagen, elastin, and fibroblast cells, which are responsible for the biosynthesis of collagen and elastin.

The epidermis itself also may be considered to consist of two major zones, an inner or malpighian layer and an outer or horny layer. The malpighian layer, a living tissue, may be further divided into basal, spinous, and granular layers. The horny layer, a dead tissue, is also referred to as stratum corneum.

In the natural process, basal cells in the basal layer move outward through the spinous and granular layers to become dead cells called corneocytes, in the stratum corneum. The stratum corneum consists of approximately 14 layers of corneocytes. In the normal skin it takes about 14 days for the basal cells to move from the basal layer to the end of the granular layer and to become corneocytes, and another 14 days to reach the outermost layer of the stratum corneum, where they are naturally shed or exfoliated. This process of forming corneocytes is called keratinization, and stratum corneum are the natural products produced by this process. The stratum corneum is the skin tissue that one feels when touching the skin. Usually, it takes about 28 days for cells of the basal layer to move outward to the surface in the course of making new skin.

It is thought that by increasing the natural desquamation rate (the cell renewal rate) of the outermost part of the stratum corneum and thus exposing lower layers of the stratum corneum, the appearance of the skin will be improved. Many substances are known to increase the rate of natural desquamation but recently compositions containing hydroxycarboxylic (alpha and beta) acids have received an increasing amount of attention.

A drawback to the use of hydroxycarboxylic acids is that they are most effective at low pHs, about 4.0 or less. It appears, however, that there exists a strong correlation between the degree of exfoliation (cell renewal rate) and the degree of irritation. Thus, at pH of about 4.0 or less, the hydroxycarboxylic acids show significant stimulation of cell renewal but also a fair degree of skin irritation. On the other hand, as the pH approaches neutral (7.0), the cell renewal rate decreases while there is little or no irritation. Thus, it would be desirable to achieve an increase in the rate of natural desquamation without further increasing the irritation of the skin. It would be most desirable to provide for enhanced skin desquamation at a neutral pH. The present invention solves that problem by providing for enhanced skin desquamation at a neutral pH without undue irritation.

SUMMARY OF THE INVENTION

In accordance with the present invention, there is provided a cosmetic or dermopharmaceutical composition for topical use comprising an ascorbic acid derivative and a carrier.

The ascorbic acid derivative is preferably an ester of ascorbic acid, a salt, or mixtures thereof. With respect to the esters, they may be selected from the group consisting of fatty acid mono-, di-, tri-, or tetra-esters of ascorbic acid. Nonlimiting examples are ascorbyl palmitate, ascorbyl laureate, ascorbyl myristate, ascorbyl stearate, ascorbyl dipalmitate, ascorbyl tripalmitate, and ascorbyl tetrapalmitate (tetrahexyldecyl ascorbate). With respect to the salts, they may be selected from the phosphates and sulfates with the cation being calcium, magnesium, sodium and the like.

The ascorbic acid derivative is preferably the salt of an ascorbic acid phosphate or sulfate, preferably a phosphate. The ascorbic acid phosphate is generally selected from L-ascorbic acid 3-phosphate, L-ascorbic acid 2-phosphate, L-ascorbic acid 3-pyrophosphate and bis (L-ascorbic acid 3,3-) phosphate. Preferably, the ascorbic acid phosphate is magnesium or sodium ascorbyl phosphate; more preferably, magnesium ascorbyl phosphate. Likewise, the ascorbic acid sulfate is generally selected from L-ascorbic acid 3-sulfate, L-ascorbic acid 2-sulfate, L-ascorbic acid 3-pyrosulfate and bis (L-ascorbic acid 3,3-) sulfate.

The ascorbic acid derivative is present in an amount effective to enhance skin cell desquamation rate beyond the naturally occurring skin cell desquamation rate. The ascorbic acid derivative enhances the rate of skin desquamation and, at the same time, does not irritate the skin to a significant degree.

In accordance with this aspect of the present invention, there is provided a composition comprising an ascorbic acid derivative present in a therapeutically effective amount in a topically acceptable vehicle for application to human skin to enhance the rate of skin desquamation beyond the rate of naturally occurring skin desquamation. In other words, this aspect contemplates the use of an ascorbic acid derivative in the preparation of a cosmetic composition to enhance the rate of skin desquamation beyond the rate of naturally occurring skin desquamation.

Generally, the composition contains from about 0.01% to about 99% of the ascorbic acid derivative. Preferably, the composition has a pH in the range from about 5.0 to about 9.0, preferably from about 6.0 to about 8.0.

Another aspect of the present invention includes a method of increasing the rate of skin exfoliation or desquamation comprising topically applying a cosmetic composition containing an amount of an ascorbic acid derivative effective to enhance the rate of skin cell desquamation beyond the naturally occurring rate of skin cell desquamation. In this aspect, the method includes topically applying to the skin a composition comprising an ascorbic acid derivative in an amount and for a period of time sufficient to increase the rate of natural skin desquamation.

DETAILED DESCRIPTION OF THE INVENTION

In accordance with the present invention, a composition acceptable for topical application to the skin comprises an ascorbic acid derivative and a carrier.

The ascorbic acid derivative useful in the present invention includes all enantiomers whether singly or in combination. Preferably, the ascorbic acid is provided in the levo form.

The ascorbic acid derivative is preferably an ester of ascorbic acid, a salt, or a mixture thereof. With respect to the esters, they may be selected from the group consisting of fatty acid mono-, di-, tri- or tetra-esters of ascorbic acid. Nonlimiting examples are ascorbyl palmitate, ascorbyl laureate, ascorbyl myristate, ascorbyl stearate, ascorbyl dipalmitate, ascorbyl dilaurate, ascorbyl dimyristate, ascorbyl distearate, ascorbyl tripalmitate, ascorbyl trilaurate, ascorbyl trimyristate, ascorbyl tristearate, ascorbyl tetrapalmitate (tetrahexyldecyl ascorbate), ascorbyl tetralaurate, ascorbyl tetramyristate, ascorbyl tetrastearate, and mixtures thereof.

With respect to the salts, they may be selected from the phosphates and sulfates, preferably phosphate. The ascorbic acid phosphate is generally selected from L-ascorbic acid 3-phosphate, L-ascorbic acid 2-phosphate, L-ascorbic acid 3-pyrophosphate and bis (L-ascorbic acid 3,3-) phosphate. Preferably, the ascorbic acid phosphate is magnesium or sodium ascorbyl phosphate; more preferably, magnesium ascorbyl phosphate. Likewise, the ascorbic acid sulfate is generally selected from L-ascorbic acid 3-sulfate, L-ascorbic acid 2-sulfate, L-ascorbic acid 3-pyrosulfate and bis (L-ascorbic acid 3,3-) sulfate.

The cation portion includes, but is not limited to alkaline earth metals such as calcium, magnesium, and sodium. They can be used alone or in a mixture of two or more.

To prepare the compositions according to the present invention, at least one of the aforementioned ascorbic acid derivatives is mixed with a pharmaceutically or cosmetically acceptable vehicle or carrier.

The compositions of the present invention may be formulated as a solution, gel, lotion, cream, ointment, oil-in-water emulsion, water-in-oil emulsion, or other pharmaceutically acceptable form. The compositions of the present invention may also contain various known and conventional cosmetic ingredients so long as they do not detrimentally affect the desired enhancement of skin desquamation.

The cosmetically acceptable vehicle acts as a dilutant, dispersant or carrier for other materials present in the composition, so as to facilitate their distribution when the composition is applied to the skin.

Vehicles other than water can include liquid or solid emollients, solvents, humectants, thickeners and powders. For example, the following vehicles can be use alone or as a combination of one or more vehicles.

Emollients, such as stearyl alcohol, glyceryl monoricinoleate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rapeseed oil, safflower seed oil, evening primrose oil, soybean oil, sunflower seed oil, avocado oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate.

As used herein, "emollients" refer to materials used for the prevention or relief of dryness, as well as for the protection of the skin. A wide variety of suitable emollients are known and may be used herein. Sagarin, Cosmetics, Science and Technology, 2nd Edition, Vol. 1, pp. 32–43 (1972), incorporated herein by reference, contains numerous examples of suitable materials. Examples of classes of useful emollients include the following:

1. Hydrocarbon oils and waxes. Examples include mineral oil, petrolatum, paraffin, ceresin, ozokerite, microcrystalline wax, polyethylene, and perhydrosqualene.
2. Silicone oils, such as dimethyl polysiloxanes, methylphenyl polysiloxanes, water-soluble and alcohol-soluble silicone glycol copolymers.
3. Triglyceride esters, for example vegetable and animal fats and oils. Examples include caster oil, safflower oil, cottonseed oil, corn oil, olive oil, cod liver oil, almond oil, avocado oil, palm oil, sesame oil, and soybean oil.
4. Acetoglyceride esters, such as acetylated monoglycerides.
5. Ethoxylated glycerides, such as ethoxylated glyceryl monostearate.
6. Alkyl esters of fatty acids having 10 to 20 carbon atoms. Methyl, isopropyl, and butyl esters of fatty acids are particularly useful herein. Examples of other useful alkyl esters include hexyl laurate, isohexyl laurate, isohexyl palmitate, isopropyl palmitate, decyl oleate, isodecyl oleate, hexadecyl stearate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.
7. Alkenyl esters of fatty acids having 10 to 20 carbon atoms. Examples include oleyl myristate, oleyl stearate, and oleyl oleate.
8. Fatty acids having 10 to 20 carbon atoms. Suitable examples include pelargonic, lauric, myristic, palmitic, stearic, isostearic, hydroxystearic, oleic, linoleic, ricinoleic, arachidic, behenic, and erucic acids.
9. Fatty alcohols having 10 to 20 carbon atoms. Lauryl, myristyl, cetyl, hexadecyl, stearyl, isostearyl, hydroxystearyl, oleyl, ricinoleyl, behenyl, and erucyl alcohols, as well as 2-octyl dodecanol, are examples of satisfactory fatty alcohols.
10. Fatty alcohols ethers. Ethoxylated fatty alcohols of 10 to 20 carbon atoms include the lauryl, cetyl, stearyl, isostearyl, oelyl, and cholesterol alcohols having attached thereto from 1 to 50 ethylene oxide groups or 1 to 50 propylene oxide groups.
11. Ether-esters such as fatty acid esters of ethoxylated fatty alcohols.
12. Lanolin and derivatives. Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases are illustrative of emollients derived from lanolin.
13. Polyhydric alcohols and polyether derivatives. Propylene glycol, dipropylene glycol, polypropylene glycols 2000 and 4000, polyoxyethylene polyoxyethylene glycols, polyoxypropylene polyoxyethylene glycols, glycerol, sorbitol, ethoxylated sorbitol, hydroxypropyl sorbitol, polyethylene glycols 200–6000, methoxy polyethylene glycols 350, 550, 750, 2000 and 5000, poly[ethylene oxide]-homopolymers (100,000–5,000,000), polyalkylene glycols and derivatives, hexylene glycol (2-methyl-2,4-pentanediol), 1,3-butylene glycol, 1,2,6-hexanetriol, ethohexadiol USP (2-ethyl-1,3-hexanediol), $C_{15}$–$C_{18}$ vicinal glycol, and polyoxypropylene derivatives of trimethylopropane are examples of this class of materials.

14. Polyhydric alcohol esters. Ethylene glycol mono and di-fatty acid esters, diethylene glycol mono- and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters for use herein.

15. Wax esters such as beeswax, spermaceti, myristyl, myristate, stearyl stearate.

16. Beeswax derivatives, e.g. polyoxyethylene sorbitol beeswax. These are reaction products of beeswax with ethoxylated sorbitol of varying ethylene oxide content, forming a mixture of ether-esters.

17. Vegetable waxes including carnauba and candelilla waxes.

18. Phospholipids, such as lecithin and derivatives.

19. Sterols. Cholesterol and cholesterol fatty acid esters are examples thereof.

20. Amides such as fatty acid amides, ethoxylated fatty acid amides, solid fatty acid alkanolamides.

Vehicles may also include propellants such as propane, isobutane, dimethyl ether, carbon dioxide, nitrous oxide; and solvents such as ethyl alcohol, isopropanol, acetone, ethylene glycol monomethyl ether, diethylene glycol monobutyl ether, diethylene glycol monoethyl ether, or powders such as chalk, talc, fullers earth, kaolin, starch, gums, collodial silica, sodium polyacrylate, tetra alkyl and/or trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, ethylene glycol monostearate.

The composition can optionally comprise suncreens such as inorganic and organic sunscreens to provide protection from the harmful effects of excessive exposure to sunlight during use of the composition of the present invention.

Examples of suitable organic sunscreens, when required, include those set out in Table 1 below, and mixtures thereof.

TABLE 1

| CTFA Name | Trade Name | Supplier |
| --- | --- | --- |
| Benzophenone-3 | UVINUL ® M-40 | BASF Chemical Co. |
| Benzophenone-4 | SPECRA-SORB ® UV-24 | American Cyanamide |
| DEA Methoxycinnamate | BERNEL HYDRO ® | Bernel Chemical |

TABLE 1-continued

| CTFA Name | Trade Name | Supplier |
| --- | --- | --- |
| Ethyl dihydroxypropyl-PABA | AMERSCREEN ® P | Amerchol Corp. |
| Glyceryl PABA | NIPA ® G.M.P.A. | Nipa Labs. |
| Homosalate | KEMESTER ® HMS | Hunko Chemical |
| Methyl anthranilate | SUNAROME ® UVA | Felton Worldwide |
| Octocrylene | UVINUL ® N-539 | BASF Chemical Co. |
| Octyl dimethyl PABA | AMERSCOL ® | Amerchol Corp |
| Octyl methoxycinnamate | PARSOL ® MCX | Bernel Chemical |
| Octyl salicylate | SUNAROME ® WMO | Felton Worldwide |
| PABA | PABA ® | National Starch |
| 2-Phenylbenzimidazole-5-sulphonic acid | EUSOLEX ® 232 | EM Industries |
| TEA salicylate | SUNAROME ® | Felton Worldwide |
| 3-(4-methylbenzylidene)-camphor | EUSOLEX ® 6300 | EM industries |
| Benzophenone-1 | UVINUL ® 400 | BASF Chemical Co. |
| Benzophenone-2 | UVINUL ® D-50 | BASF Chemical Co. |
| Benzophenone-6 | UVINUL ® D-49 | BASF Chemical Co. |
| Benzophenone-12 | UVINUL ® 408 | BASF Chemical Co. |
| 4-Isopropyl dibenzoyl methane | EUSOLEX ® 8020 | EM Industries |
| Etocrylene | UVINUL ® | BASF Chemical Co. |

The composition of the invention can accordingly comprise from 0.1 to 10%, preferably from 1 to 5% by weight of an organic sunscreen material.

Inorganic sunscreen

The composition optionally can also comprise as a sunscreen titanium dioxide, zinc oxide, having an average particle size of from 1 to 300 nm, iron oxide, having an average particle size of from 1 to 300 nm, silica, such as fumed silica, having an average particle size of from 1 to 100 nm. It should be noted that silica, when used as an ingredient in the emulsion according to the invention can provide protection from infrared radiation.

Ultrafine titanium dioxide in either of two forms, namely water-dispersible titanium dioxide and oil-dispersible titanium dioxide may be used. Water-dispersible titanium dioxide is ultrafine titanium dioxide, the particles of which are uncoated or which are coated with a material to impart a hydrophilic surface property to the particles. Examples of such materials include aluminum oxide and aluminum silicate. Oil-dispersible titanium dioxide is ultrafine titanium dioxide, the particles of which exhibit a hydrophobic surface property, and which, for this purpose, can be coated with metal soaps such as aluminum stearate, aluminum laurate or zinc stearate, or with organosilicone compounds.

By "ultrafine titanium dioxide" is meant particles of titanium dioxide having an average particle size of less than 100 nm, preferably from 10 to 40 nm and most preferably from 15 to 25 nm. The total amount of titanium dioxide that can optionally can be incorporated in the composition according to the invention is from 1 to 25%, preferably from 2 to 10% and ideally from 3 to 7% by weight of the composition.

Optional Skin Benefit Materials and Cosmetic Adjuncts

A particularly convenient form of the composition is an emulsion, in which case an oil or oily material (emollient) will normally be present, together with an emulsifier to provide either a water-in-oil emulsion or an oil-in-water emulsion, depending largely on the average hydrophilic-lypophilic balance (HLB) of the emulsifier employed. When a water-in-oil emulsion is required, the chosen emulsifier or emulsifiers should normally have an average HLB value of from 1 to 6. When an oil-in-water emulsion is required, a chosen emulsifier or emulsifiers should have an average HLB value of >6.

Examples of suitable emulsifiers are set below in Table 2 in which the chemical name of the emulsifiers is given together with an example of a trade name as commercially available, and the average HLB value.

TABLE 2

| Chemical Name of Emulsifier | Trade Name | HLB Value |
|---|---|---|
| Sorbitan trioleate | Arlacel ® 85 | 1.8 |
| Sorbitan trioleate | Span ® 65 | 2.1 |
| Glycerol monooleate | Aldo ® MD | 2.7 |
| Glycerol monostearate | Atmul ® 84S | 2.8 |
| Glycerol monolaurate | Aldo ® MC | 3.3 |
| Sorbitan sesquioleate | Arlacel ® 83 | 3.7 |
| Sorbitan monooleate | Arlacel ® 80 | 4.3 |
| Sorbitan monostearate | Arlacel ® 60 | 4.7 |
| Poloxyethylene (2) stearyl ether | Brij ® 72 | 4.9 |
| Poloxyethylene sorbitol beeswax derivative | G-1702 | 5 |
| PEG 200 dilaurate | Emerest ® 2622 | 6.3 |
| Sorbitan monopalmitate | Arlacel ® 40 | 6.7 |
| Polyoxyethylene (3.5) nonyl phenol | Emulgen ® 903 | 7.8 |
| PEG 200 monostearate | Tegester ® PEB 200 MS | 8.5 |
| Sorbitan monolaurate | Arlacel ® 200 | 8.6 |
| PEG 400 dioleate | Tegester ® PEG 400-DO | 8.8 |
| Polyoxyethylene (5) monostearate | Ethofat ® 60-16 | 9.0 |
| Polyoxyethylene (4) sorbitan Monostearate | Tween ® 61 | 9.6 |
| Polyoxyethylene (4) lauryl ether | Brij ® 30 | 9.7 |
| Polyoxyethylene (5) sorbitan Monooleate | Tween ® 81 | 10.0 |
| PEG 300 monooleate | Neutronyx ® 834 | 10.4 |
| Polyoxyethylene (20) sorbitan tristearate | Tween ® 65 | 10.5 |
| Polyoxyethylene (20) sorbitan trioleate | Tween ® 85 | 11.0 |
| Polyoxyethylene (8) monostearate | Myrj ® 45 | 11.1 |
| PEG 400 monooleate | Emerest ® 2646 | 11.7 |
| PEG 400 monostearate | Tegester ® PEG 400 | 11.9 |
| Polyoxyethylene 10 monooleate | Ethofat ® 0/20 | 12.2 |
| Polyoxyethylene (10) stearyl ether | Brij ® 76 | 12.4 |
| Polyoxyethylene (10) cetyl ether | Brij ® 56 | 12.9 |
| Polyoxyethylene (9.3) octyl phenol | Triton ® X-100 | 13.0 |
| Polyoxyethylene (4) sorbitan monolaurate | Tween ® 21 | 13.3 |
| PEG 600 monooleate | Emerest ® 2660 | 13.7 |
| PEG 1000 dilaurate | Kessco ® | 13.9 |
| Polyoxyethylene sorbitol lanolin derivative | G-1441 | 14.0 |
| Polyoxyethylene (12) lauryl ether | Ethosperse ® LA-12 | 14.4 |
| PEG 1500 dioleate | Pegosperse ® 1500 | 14.6 |
| Polyoxyethylene (14) laurate | Arosurf ® HFL-714 | 14.8 |
| Polyoxyethylene (20) sorbitan monostearate | Tween ® | 14.9 |
| Polyoxyethylene 20 sorbitan monooleate | Tween ® 80 | 15.0 |
| Polyoxyethylene (20) stearyl ether | Brij ® 78 | 15.3 |
| Polyoxyethylene (20) sorbitan monopalmitate | Tween ® 40 | 15.6 |
| Polyoxyethylene (20) cetyl ether | Brij ® 58 | 15.7 |
| Polyoxyethylene (25) oxypropylene monostearate | G-2162 | 16.0 |
| Polyoxyethylene (20) sorbitol monolaurate | Tween ® 20 | 16.7 |
| Polyoxyethylene (23) lauryl ether | Brij ® 35 | 16.9 |
| Polyoxyethylene (50) monostearate | Myrj ® 53 | 17.9 |
| PEG 4000 monostearate | Pegosperse ® 4000 MS | 18.7 |

It is to be understood that two or more emulsifiers can be employed if desired. The amount of emulsifier or mixtures thereof, that optionally can be incorporated in the composition is from 1 to 50%, preferably from 2 to 20% and most preferably from 2 to 10% by weight of the composition.

Water

The composition can also comprise water, usually up to 95%, preferably from 5 to 95% by weight.

Silicone Surfactant

The composition can also optionally comprise a high molecular weight silicone surfactant that can also act as an emulsifier, in place of or in addition to the option emulsifier(s) already mentioned.

The silicone surfactant is a high molecular weight polymer of dimethyl polysiloxane with polyoxethylene and/or polyoxpropylene side chains having a molecular weight of from 10,000 to 50,000 and having the structure:

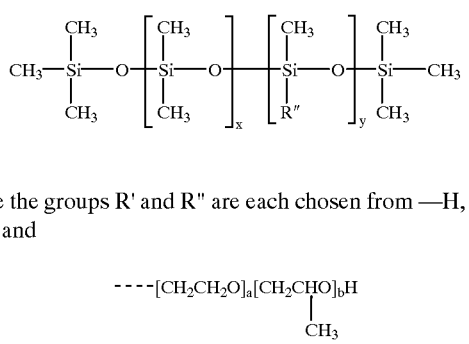

where the groups R' and R" are each chosen from —H, $C_{1-18}$ alkyl and $$----[CH_2CH_2O]_a[CH_2CHO]_bH$$
$$\quad\quad\quad\quad\quad\quad\quad\quad\quad |$$
$$\quad\quad\quad\quad\quad\quad\quad\quad\quad CH_3$$

where the groups R' and R" are each chosen from -H, $C_{1-18}$ alkyl and a has a value of from 9 to 115, b has a value of from 0 to 50, x has a value of from 133 to 673, y has a value of from 25 to 0.25.

Preferably, the dimethyl polysiloxane polymer is one in which:

a has a value of from 10 to 114, b has a value of from 0 to 49, x has a value of from 388 to 402, y has a value of from 15 to 0.75.

one of groups R' and R" being lauryl, and the other having a molecular weight of from 1000 to 5000.

A particularly preferred dimethyl polysiloxane polymer is one in which:

a has the value 14, b has the value 13, x has the value 249, y has the value 1.25.

The dimethyl polysiloxane polymer is conveniently provided as a dispersion in a volatile siloxane, the dispersion comprising, for example, from 1 to 20% by volume of the polymer and from 80 to 99% by volume of the volatile siloxane. Ideally, the dispersion consists of a 10% by volume of the polymer dispersed in the volatile siloxane.

Examples of the volatile siloxanes in which the polysiloxane polymer can be dispersed include polydimethyl siloxane (pentamer and/or hexamer).

A particularly preferred silicone surfactant is cyclomethicone and dimethicone copolyol, such as DC 3225C Formulation Aid available from DOW CORNING. Another is laurylmethicone copolyol, such as DC Q2-5200, also available from Dow Corning.

The amount of silicone surfactant, when present in the composition will normally be up to 25%, preferably from 0.5 to 15% by weight of the emulsion.

Other Cosmetic Adjuncts

Examples of conventional adjuncts which can optionally be employed include preservatives, such as para-hydroxy benzoate esters; antioxidants, such butyl hydroxy toluene; humectants, such as glycerol, ethoxylated glycerins such as glycereth-26, sorbitol, 2-pyrrolidone-5-carboxylate, dibutylphthalate, gelatin, polyethylene glycol, such as PEG 200–600; buffers together with a base such as triethanolamine or sodium hydroxide; waxes, such as beeswax, ozokerite wax, paraffin wax; plant extracts, such as Aloe Vera, cornflower, witch hazel, elderflower, cucumber; as well as acerola cherry fermentate, thickeners; activity enhancers; colorants; and perfumes. Cosmetic adjuncts can form the balance of the composition.

It may also be desirable to incorporate anti-inflammatory and/or anti-irritant agents. The natural anti-inflammatory and/or anti-irritant agents are preferred. For example, licorice and its extracts, dipotassium glycyrrhizinate, oat and oat extracts, candelilla wax, alpha bisabolol, aloe vera, Manjistha (extracted from plants in the genus Rubia, particularly *Rubia cordifolial*), and Guggal (extracted from plants in the genus Commiphora, particularly *Commiphora Mukul*), may be used.

Additional skin benefit agents such as ceramides, glycoceramides, pseudoceramides, sphingolipids such as sphingomyelins, cerebrosides, sulphatides, and ganglioside, sphingosines, dihydrosphingosine, phytosphingosines, phospholipids, may also be incorporated, either separately or in mixtures. Fatty acids may also be combined with these skin benefit agents. For example, the ceramides and glycoceramides include those described in U.S. Pat. No. 5,589,178, 5,661,118, and 5,688,752, the relevant portions of which are incorporated herein by reference. For example, the pseudoceramides include those described in U.S. Pat. Nos. 5,198,210; 5,206,020; and 5,415,855, the relevant disclosures of which are incorporated herein by reference.

In accordance with one aspect of the present invention, the rate of natural skin desquamation may be increased by topical application to the skin of the compositions according to the present invention. In this regard, the present invention encompasses a method of enhancing the rate of natural skin desquamation comprising topically applying to the skin a composition comprising an ascorbic acid derivative in an amount and for a period of time sufficient to increase the rate of natural skin desquamation. Preferably, the composition is as described above.

Generally, the topical application is on at least a daily basis and may be applied for any suitable period of time. Within a few days, a user may notice improvement in skin texture and smoothness.

The following are illustrative examples of formulations and compositions according to this invention. Although the examples use only selected compounds and formulations, it should be understood that the following examples are illustrative and not limited.

Table 3 sets forth a preferred embodiment of the present invention.

TABLE 3

| INGREDIENT | AMOUNT (wt %) |
| --- | --- |
| Water | 82.83 |
| Magnesium ascorbyl Phosphate | 3.00 |
| Cosmetic adjuncts | 14.17 |

Table 4 presents several examples of solution and/or gel formulas falling within the scope of the present invention with the amounts provided being expressed as weight percent.

TABLE 4

| Ingredients | A | B | C | D | E | F | G |
| --- | --- | --- | --- | --- | --- | --- | --- |
| Water | 81.50 | 85.95 | 80.00 | 82.05 | 90.00 | 72.45 | 79.46 |
| SAP |  | 3.00 |  | 1.50 |  | 2.50 |  |
| MAP | 3.00 |  | 3.00 | 1.00 | 3.00 | 1.50 | 3.00 |
| Butylene Glycol | 1.50 | 1.00 | 1.00 | 2.00 | 1.50 | 7.00 | 2.00 |
| PEG-8 | 2.00 |  |  |  |  |  |  |
| Glycerin | 1.50 | 2.00 |  | 4.00 | 1.50 | 3.00 | 2.00 |
| Glycereth-26 | 2.00 | 2.00 |  |  |  | 2.00 | 4.00 |
| Sorbitol |  |  | 2.00 |  |  |  |  |
| Sodium Hyaluronate (0.5% soln) | 1.00 | 1.00 | 2.00 | 0.50 | 0.25 |  |  |
| Dipotassium Glycyrrhizinate | 0.01 | 0.05 |  |  | 0.02 |  | 0.05 |
| Panthenol |  | 0.05 | 0.05 |  | 0.05 |  | 0.02 |
| Sodium Citrate | 1.00 | 1.00 | 1.25 | 1.00 | 0.10 | 1.25 | 1.25 |
| Tetrasodium EDTA | 0.20 | 0.20 | 0.20 | 0.10 | 0.10 | 0.10 | 0.20 |
| Oat Extract |  | 0.50 | 1.00 | 0.50 |  |  |  |
| Cucumber Extract | 1.00 |  | 0.50 | 1.00 |  |  | 1.50 |
| Alcohol | 2.00 |  | 8.00 |  | 2.00 |  |  |
| Thickeners, extracts, preservatives, emulsifiers, skin conditioners, neutralizers | 3.29 | 3.25 | 1.00 | 6.35 | 1.48 | 10.20 | 6.52 |
| Total | 100.00 | 100.00 | 100.00 | 100.00 | 100.00 | 100.00 | 100.00 |

Table 5 presents several examples of emulsion, cream, and or lotion formulas falling within the scope of the present invention with the amounts provided being expressed as weight percent.

The increase in skin cell renewal rate, irritation level and therapeutic index were measured substantially according to the procedure described in *Soap/Cosmetics/Chemical Specialties for September* 1993 at pp. 54–58 and 76. The results are set forth in Table 7.

TABLE 5

| Ingredients | A | B | C | D | E | F | G |
|---|---|---|---|---|---|---|---|
| Water | 70.05 | 67.00 | 58.46 | 57.25 | 38.00 | 54.35 | 79.70 |
| SAP | | 3.00 | | 1.50 | | 3.00 | |
| MAP | 3.00 | | 3.00 | 1.50 | 1.50 | 1.50 | 2.00 |
| Butylene Glycol | | 4.00 | 4.00 | 3.00 | 3.50 | 5.00 | |
| Glycerin | | 0.50 | | 3.00 | | | 2.00 |
| Glycereth-26 | 2.00 | | 1.00 | | | | |
| Sorbitol | | | | | 1.00 | | |
| Sodium Hyaluronate (0.5% soln) | | 0.50 | 1.00 | | 0.50 | 1.00 | |
| Allantoin | 0.10 | | | | | | |
| Dipotassium Glycrrhizinate | 0.01 | | 0.02 | | 0.05 | | |
| Panthenol | 0.05 | 0.10 | 0.10 | | | | |
| C12–15 Alkyl Benzoate | 5.00 | 3.40 | 1.50 | | 2.50 | 6.00 | |
| Tocopherol | | 0.10 | 0.10 | 0.10 | 0.10 | | |
| Dimethicone | | 1.00 | 0.50 | 0.50 | | 0.50 | 0.25 |
| Cyclomethicone | 2.00 | | | 17.50 | 12.50 | 3.00 | |
| Isopropyl Myristate | | 1.50 | | | | 2.00 | 4.00 |
| Caprylic/Capric Triglyceride | | 3.00 | 8.00 | 5.00 | 3.50 | 1.00 | 6.00 |
| Octyl Methoxycinnamate | | | 7.00 | | 5.00 | | |
| Stearyl Glycyrrhetinate | | | | | | 0.10 | |
| GMS & PEG-100 Stearate | 4.25 | 5.00 | 5.00 | 6.00 | | 2.00 | |
| Cetyl Alcohol | 0.25 | | 1.00 | 3.00 | 3.00 | | 3.00 |
| Behenyl Alcohol | | 2.50 | | | 1.50 | 2.75 | 0.50 |
| Silica | 2.00 | | | | 0.50 | | |
| Titanium Dioxide | | 0.20 | 3.00 | | 2.50 | | |
| Sodium Citrate | 0.50 | 2.50 | 2.50 | | | 0.50 | 0.80 |
| Tetrasodium EDTA | 0.10 | 0.10 | 0.20 | 0.10 | 0.10 | 0.10 | |
| Oat Extract | 1.00 | | | | | | |
| Cucumber Extract | 0.25 | 0.75 | 1.00 | | | 0.50 | |
| Phospholipids, Sphingolipids, Cholesterol | 0.0035 | 0.004 | | | 0.005 | | |
| Thickeners, extracts, preservatives, emulsifiers, skin conditioners, neutralizers | 9.4365 | 4.846 | 2.62 | 1.55 | 24.245 | 16.70 | 1.75 |
| Total | 100.0000 | 100.000 | 100.00 | 100.00 | 100.000 | 100.00 | 100.00 |

The following examples illustrate, but do not limit, the present invention. Unless otherwise indicated, all parts and percentages are by weight.

EXAMPLE 1

In order to determine whether compositions containing ascorbic acid derivatives according to the present invention were therapeutically effective in enhancing the natural rate of skin desquamation the following tests were conducted at Dermac Laboratory, Inc. (Stamford, Conn.). Several compositions were prepared. Table 6 identifies the active skin cell renewal agent in each composition.

TABLE 6

| Ingredient | A (wt %) | B (wt %) | C (wt %) | D (wt %) | E (wt %) |
|---|---|---|---|---|---|
| Lactic acid | 5 | 3.0 | — | — | — |
| Glycolic acid | — | 3.0 | — | — | — |
| Salicylic acid | — | 0.2 | — | — | — |
| Magnesium ascorbyl phosphate | — | — | 3 | 3 | 3 |

TABLE 7

| Test Material | pH | % Increase Cell Renewal | Irritation Level | Therapeutic Index |
|---|---|---|---|---|
| A | 3.0 | 34.2 | 18.4 | 18.6 |
| B | 3.85 | 30.9 | 15.3 | 20.2 |
| C | 7.04 | 15.1 | 9.25 | 16.3 |
| D | 7.04 | 17.8 | 7.85 | 22.7 |
| E | 7.04 | 23 | 8.5 | 27.1 |

The results show that the presence of the ascorbic acid derivative surprisingly and unexpectedly increased cell renewal rate while maintaining or reducing irritation to levels substantially below that of known cell renewal actives.

EXAMPLE 2

Several compositions were prepared. Table 8 identifies the active skin cell renewal agent in each composition. The increase in skin cell renewal rate, irritation level and therapeutic index were measured according to the procedure described in Example 1. The results are set forth in Table 9.

TABLE 8

| Formula | 3% MAP | 1.5% MAP | 3% SAP | 5% lactic | 3% lactic | 3% glycolic | 0.5% salicylic |
|---|---|---|---|---|---|---|---|
| F | X | | | | | | |
| G emulsion | X | | | | | | |
| H (emulsion) | X | | | | | | |
| I | | X | | | | | |
| J | | | X | | | | |
| K | | | X | | | | |
| L | | | | X | | | |
| M | | | | | X | X | X |
| N | X | | | | | | |
| O | X | | | | | | |
| P | X | | | | | | |

TABLE 9

| Test Material | pH | % Increase Cell Renewal | Irritation Level | Therapeutic Index |
|---|---|---|---|---|
| F | 7.04 | 17.1 | 10 | 17.1 |
| G | 7.7 | 20.2 | 6.8 | 29.7 |
| H | 6.85 | 20.3 | 8.3 | 24.45 |
| I | 7.0 | 15.4 | 9.9 | 15.55 |
| J | 7.0 | 19.1 | 8.6 | 22.2 |
| K | 7.0 | 14.6 | 7.9 | 18.48 |
| L | 3.0 | 31.8 | 18.7 | 17 |
| M | 3.9 | 26.3 | 8.5 | 30.9 |
| N | 7.13 | 17.5 | 6.7 | 26.11 |
| O | 7.28 | 23.7 | 10.2 | 23.3 |
| P | 7.19 | 20.3 | 11.5 | 17.7 |

The results show that the presence of the ascorbic acid derivative surprisingly and unexpectedly increased cell renewal rate while maintaining or reducing irritation to levels substantially below that of known cell renewal actives.

It should be understood that a wide range of changes and modifications can be made to the compositions and methods of this invention. It is therefore intended that the foregoing description illustrates rather than limits this invention, and that it is the following claims, including all equivalents, which define this invention.

What is claimed is:

1. A method of enhancing the rate of mammalian skin exfoliation comprising topically applying to the skin a composition comprising a therapeutically effective amount of an ascorbic acid derivative selected from the group consisting of fatty acid esters, phosphate salts, sulfate salts, and mixtures thereof, and a Pharmaceutically acceptable carrier, wherein the composition has a pH from about 5.0 to about 8.0.

2. The method of claim 1 wherein the ascorbic acid derivative is an ester of ascorbic acid selected from the group consisting of fatty acid monoesters, fatty acid diesters, fatty acid triesters, fatty acid tetraesters, and mixtures thereof.

3. The method of claim 1 wherein the ascorbic acid derivative is an ester of ascorbic acid selected from the group consisting of ascorbyl palmitate, ascorbyl laurate, ascorbyl myristate, ascorbyl stearate, ascorbyl dipalmitate, ascorbyl dilaurate, ascorbyl dimyristate, ascorbyl distearate, ascorbyl tripalmitate, ascorbyl trilaurate, ascorbyl trimyristate, ascorbyl tristearate, ascorbyl tetrapalmitate, ascorbyl tetralaurate, ascorbyl tetramyristate, ascorbyl tetrastearate, and mixtures thereof.

4. The method of claim 1 wherein the ascorbic acid derivative is a salt of ascorbic acid selected from the group consisting of ascorbyl phosphate, ascorbyl sulfate, and mixtures thereof.

5. The method of claim 1 wherein the ascorbic acid derivative is a salt of ascorbic acid selected from the group consisting of L-ascorbic acid 3-phosphate, L-ascorbic acid 2-phosphate, L-ascorbic acid 3-pyrophosphate, bis (L-ascorbic acid 3,3-) phosphate, L-ascorbic acid 3-sulfate, L-ascorbic acid 2-sulfate, L-ascorbic acid 3-pyrosulfate, bis (L-ascorbic acid 3,3-) sulfate, and mixtures thereof.

6. The method of claim 4 wherein the salt of ascorbic acid has a cation selected from the group consisting of calcium, magnesium, sodium, and mixtures thereof.

7. The method of claim 1 wherein the ascorbic acid derivative is selected from the group consisting of magnesium ascorbyl 2-phosphate, magnesium ascorbyl 3-phosphate, and mixtures thereof.

8. The method of claim 1 wherein the composition is formulated as a solution, gel, lotion, cream or ointment.

9. The method of claim 1 wherein the composition is topically applied in an amount and for a period of time sufficient to enhance the rate the skin desquamation.

10. The method of claim 1 wherein the topical application is on at least a daily basis.

11. The method of claim 1 wherein the ascorbic acid derivative is present in an amount from about 0.01% to about 99% by weight of the composition.

* * * * *